(12) United States Patent
Wolf et al.

(10) Patent No.: US 9,226,904 B2
(45) Date of Patent: *Jan. 5, 2016

(54) PHARMACOLOGICAL TREATMENT OF PARKINSON'S DISEASE

(75) Inventors: William A. Wolf, Wheaton, IL (US);
Erik D. Istre, Saint Louis Park, MN (US)

(73) Assignee: The United States of America as Represented by the Department of Veterans Affairs, Washington, DC (US)

(*) Notice: Subject to any disclaimer, the term of this patent is extended or adjusted under 35 U.S.C. 154(b) by 422 days.

This patent is subject to a terminal disclaimer.

(21) Appl. No.: 12/730,972

(22) Filed: Mar. 24, 2010

(65) Prior Publication Data
US 2010/0179171 A1    Jul. 15, 2010

Related U.S. Application Data

(63) Continuation of application No. 11/713,156, filed on Feb. 28, 2007.

(60) Provisional application No. 60/777,939, filed on Feb. 28, 2006.

(51) Int. Cl.
| A61K 31/198 | (2006.01) |
| A61K 31/496 | (2006.01) |
| A61K 31/137 | (2006.01) |
| A61K 31/55  | (2006.01) |
| A61K 31/497 | (2006.01) |
| A61K 45/06  | (2006.01) |

(52) U.S. Cl.
CPC ............ *A61K 31/137* (2013.01); *A61K 31/198* (2013.01); *A61K 31/496* (2013.01); *A61K 31/497* (2013.01); *A61K 31/55* (2013.01); *A61K 45/06* (2013.01)

(58) Field of Classification Search
CPC .......................... A61K 31/496; A61K 31/198
USPC ............................................. 514/254.11, 567
See application file for complete search history.

(56) References Cited

U.S. PATENT DOCUMENTS

| 4,772,604 | A | 9/1988 | van Wijngaarden et al. |
| 4,782,061 | A | 11/1988 | Kruse et al. |
| 4,833,142 | A | 5/1989 | Hartog et al. |
| 4,889,852 | A | 12/1989 | Hartog et al. |
| 5,424,313 | A | 6/1995 | Hartog et al. |
| 5,462,942 | A | 10/1995 | Hartog et al. |
| 5,710,149 | A | 1/1998 | Cliffe |
| 5,712,270 | A | 1/1998 | Sabb ............................ 514/212 |
| 6,251,908 | B1 | 6/2001 | Bottcher et al. |
| 6,300,329 | B1 | 10/2001 | McLean et al. |
| 6,518,272 | B2 | 2/2003 | Childers et al. ......... 514/252.16 |
| 6,521,623 | B1 | 2/2003 | Cereda et al. ............ 514/252.19 |
| 6,608,064 | B2 | 8/2003 | McClean et al. ............... 514/249 |
| 6,916,823 | B2 | 7/2005 | Mailman et al. ............... 514/284 |
| 6,967,201 | B1 | 11/2005 | Briner et al. |
| 7,504,395 | B2 | 3/2009 | Brunner et al. |
| 2002/0177616 | A1 | 11/2002 | Fahrig et al. ................... 514/373 |
| 2003/0186838 | A1 | 10/2003 | Feenstra et al. |
| 2004/0147581 | A1* | 7/2004 | Taylor et al. ................... 514/406 |
| 2004/0198753 | A1* | 10/2004 | Kase et al. ................. 514/263.2 |
| 2005/0239797 | A1 | 10/2005 | Gaster et al. ............. 514/253.03 |
| 2006/0004023 | A1 | 1/2006 | Brunner et al. |
| 2009/0156581 | A1 | 6/2009 | Dillon et al. ............. 514/217.02 |
| 2011/0178178 | A1 | 7/2011 | Brotchie et al. |

FOREIGN PATENT DOCUMENTS

| DE | EP 1 256 343 | 7/2006 |
| EP | 1339398 | 9/2008 |
| WO | WO9313766 | 7/1993 |
| WO | 9707120 | 2/1997 |
| WO | 9842344 | 10/1998 |
| WO | 9914213 | 3/1999 |
| WO | 0114330 | 3/2001 |
| WO | WO 01/68063 | 9/2001 |
| WO | 02066473 | 8/2002 |
| WO | WO 02/092088 | 11/2002 |
| WO | WO 2006/113485 | 10/2006 |
| WO | WO 2007/064586 | 6/2007 |
| WO | WO2009/156380 | * 12/2009 |

OTHER PUBLICATIONS

Milan et al. (J Pharm Exper Therap, 268 (1): 337-352, 1993).*
Ivarani et al. (Journal of Neuroscience, 23 (27): 9107-9115, 2003).*
Ahlskog et al., "Adjunctive Cabergoline Therapy of Parkinson's Disease: Comparison with Placebo and Assessment of Dose Responses and Duration Effect", *Clinical Neuropharmacology*, 202-212 (1996).
Bara-Jimenez et al., "Effects of serotonin 5-HT1A agonist in advanced Parkinson's disease," *Mov Disord*, 2o: 932-936 (2005).
Bezard, "A Call for Clinically Driven Experimental Design in Assessing Neuroprotection in Experimental Parkinsonism," *Behav. Pharmacol.*, 17(5-6): 379-382 (2006).
Bibbiani et al., Serotonin 5-HT1A agonist improves motor complications in rodent and primate parkinsonian models, *Neurology*, 57: 1829-34, (2001).
Bishop and Walker, "Combined intrastriatal dopamine D1 and serotonin 5-HT2 receptor stimulation reveals a mechanism for hyperlocomotion in 6-hydroxydopamine-lesioned rats," *Neuroscience*, 121: 649-657 (2003).
Carta et al., "Dopamine Released from 5-HT Terminals is the Cause of L-DOPA-induced Dyskinesia in Parkinsonian Rats" *Brian* 130: 1819-1833 (2007).
Clarke et al., "Cabergoline for Levodopa-Induced Complications in Parkinson's Disease", *Cocherane Database of Systematic Review* (2001).
Fici, G.J. et al., "D1 Dopamine Receptor Activity of Anti-Parkinsonian Drugs,", *Life Sciences*, 6o (18): 1597-1603 (1997).
Gnanalingham et al., "The Differential Behavioural Effects of Benzazephine D1 Dopamine Agonists with Varying Efficacies, Co-administered with Quinpirole in Primate and Rodent Models of Parkinson's Disease," 177: 287-297 (1995).

(Continued)

*Primary Examiner* — Bong-Sook Baek
(74) *Attorney, Agent, or Firm* — Klauber & Jackson LLC

(57) ABSTRACT

The present invention relates to the co-administration of two neurotransmitter agonists to patients with motor disorders, for the purpose of symptom reduction. In particular the present invention provides methods and compositions for alleviation of akinesia, rigidity and/or tremor associated with Parkinson's disease.

5 Claims, 7 Drawing Sheets

(56) References Cited

OTHER PUBLICATIONS

Goetz et al., "Sarizotan as a treatment for dyskinesias in Parkinson's disease: a double-blind placebo-controlled trial," *Mov Disord*, 22: 179-186 (2007).

Gomez-Mancilla et al., "Effects of Nondopaminergic Drugs on L-DOPA-Induced Dyskinesias in MPTP-Treated Monkeys" *Clinical Neuropharmacology*, 16(5): 418-427 (1993).

Gulwadi et al., "Dinapsoline: characterization of a D1 dopamine receptor agonist in a rat model of Parkinson's disease," *J Pharmacol Exp Ther*, 296: 338-344 (2001).

Guttman et al., "Current concepts in the diagnosis and management of Parkinson's disease," *CMAJ*, 168: 293-301 (2003).

Iravani et al., "3,4-Methylenedioxymethamphetamine (Extasy) Inhibits Dyskinesia Expression and Normalizes Motor Activity in 1-Methyl-4-Phenyl-1,2,3,6-Tetrahydropyridine-Treated Primates", *The Journal of Neuroscience*, 23(27): 9107-9115 (2003).

Iravani et al., "In 1-Methyl-4-phenyl-1,2,3,6-tetrahydropyridine-Treated Primates, the Selective 5-Hydrooxytryptamine 1a Agonist ®-(+)-8-OHDPAT Inhibits Levodopa-Induced Dyskinesia but only with Increased Motor Disability" *The Journal of Pharmacology and Experimental Therapeutics*, 319(3): 1225-1234 (2006).

Jackson et al., "Time course of bromocriptine induced excitation in the rat: behavioural and biochemical studies," *Naunyn Schmiedebergs Arch Pharmacol*, 351: 146-155 (1995).

Jackson et al., "Effect of 5-HT 1B/D Receptor Agonist and Antagonist Administration on Motor Function in Haloperidol and MPTP-Treated Common Marmoses," *Pharmocology, Biochemistry and Behavior*, 79: 391-400 (2004).

Juncos and Delong, "Parkinson disease and basal ganglia movement disorders," in Dale and Federman (eds.), *WebMD Scientific American Medicine*, NY: WebMD Corporation, Chapter 11, Section 15, pp. 1-21 (2001).

Kannari et al., "Activation of 5-HT1A but not 5-HT1B Receptors Attenuates and Increase in Extracellular Dopamine Dericed from Exogenously Administered L-DOPA in the Striatim with Nigrostriatal Denervation," *Journal of Neurochemistry*, 76: 1346-1353 (2001).

Kazuya et al., "Tandospirone Cirate, A Selective 5-HT1A Agonist, Alleviated L-DOPA-Induced Dyskinesia in Patients with Parkinson's Disease," *Braine Nerve*, Accession No. 02A0253880, pp. 133-137 (2002).

Knobelman et al., "Regulations of Extracellular Concentrations of 5-Hydroxytryptamine (5-HT) in Mouse Stiatum by 5-HT1A and 5-HT1B Receptors," *The Journal of Pharmacology and Experimental Therapeutics*, 292 (3): 1111-1117 (2000).

Lieberman et al., "Lisuride combined with levodopa in advanced Parkinson disease," *Neurology*, 31: 1466-1469 (1981) abstract only.

Mignon et al., "Postsynaptic 5-HT$_{1A}$ receptors mediate an increase in locomotor activity in the monoamine-depleted rat," *Psychopharmacology*, 163:85-94 (2002).

Mignon et al., "8-Hydroxy-2-(di-n-propylamino) Tetralin Reduces Striatal Glumate in an Animal Model of Parkinson's Disease," *Neuroreport*, 16(7): 699-703 (2005).

Mignon et al., "Postsynaptic 5-HT$_{1A}$ receptor stimulation increases motor activity in the 6-hydroxydopamine-lesioned rat: implications for treating Parkinson's disease," *Psychopharmacology*, 192:49-59 (2007).

Missale, C. et al., "Dopamine: From Structure to Function," *Physiological Reviews*, 78 (1): 189-225 (1998).

Newman-Tancredi et al., "Differential Actions of Antiparkinson Agents at Multiple Classes of Monoaminergic Receptor III Agonist and Antagonist Properties at Serotonin, 5-HT1 and 5-HT2, Receptor Subtypes," *The Journal of Pharmacology and Experimental Therapeutics*, 303 (2): 815-822 (2002).

Nicholson et al. "5-Hydroxytryptamine (5-HT, Serotonin) and Parkinson's Disease—Opportunities for Novel Therapeutics to Reduct the Problems of Levodopa Therapy", *European Journal of Neurology*, 9 (3): 1-6 (2002).

Olanow et al., "Multicenter, Open-Label, Trial of Sarizotan in Parkinson Disease Patients with Levodopa-Induced Dyskinesias (the SPLENDID Study)," *Clinical Neuropharmacology*, 27 (2): 58-62 (2004).

Parkinson's Disease Foundation, Symptoms of Parkinson's Disease, 2010 (http://www.pdf.org/en/symptoms).

Pearce et al., "Actions of the D1 agonists A-77636 and A-86929 on locomotion and dyskinesis in MPTP-treated L-DOPA-primed common marmosets," *Psychopharmacol*,142: 51-60, (1999).

PDF copy regarding ALS from "MedicineNet.com", (Apr. 30, 2009).

PDF copy regarding motor neuron diseases from "MedicineNet. com", (Apr. 28, 2009).

Protais et al., "Similar Pharmacology Properties of 8-OH-DPAT and Alnespirone (S 20499) at Dopamine Receptors: Comparison with Buspirone," 352: 179-187 (1998).

Rascol et al., "Induction by dopamine D1 receptor agonist ABT-431 of dyskinesia similar to levodopa in patients with Parkinson disease,"*Ann Neurol*, 45: 736-741 (1999).

Riad et al., "Somatodendritic Localization of 5-HT1A and Preterminal Axonal Localization of 5-HT1B Serotonin Receptors in the Adult Rat Brain," *The Journal of Comparative Neurology*, 417: 181-194 (2000).

Rouillard et al., "Effects of Chronic Treatment of MPTP Monkeys with Bromocriptine Alone or in Combination with SKF 38393," 185: 209-215 (1990).

Schapira et al., "Novel-Pharmacological Targets for the Treatment of Parkinson's Disease," *Nature Reviews*, 5: 845-854 (2006).

Schutz-Mignon, "Regulation of Basal Ganglia Circuitry by a 5-HT1A Agonist: Revelence to Parkinson's Disease," *Dissertation*, Jan. 2002.

Schwarting and Huston, "The unilateral 6-hydroxydopamine lesion model in behavioral brain research: analysis of functional deficits, recovery and treatments," *Frog Neurobiol*, 50: 275-331(1996).

Sijbesma et al., "The Anti-Aggressive Drug Eltoprazine Preferentially Binds to 5-HT1A and 5-HT1B Receptor Subtypes in Rat Brian: Sentivity to Guanine Nucleotides," *European Journal of Pharmacology*, 187 (2): 209-223 (1990).

Sprouse et al., "Electrophysiological Responses of Serotoninergic Dorsal Raphe Neorons to 5-HT1A and 5-HT1B Agonists," *Synapse*, 1: 3-9 (1987).

Tomiyama et al., "A serotonin 5-HT$_{1A}$ receptor agonist prevents behavioral sensitization to L-DOPA in a rodent model of Parkinson's disease," *Neurosci Res*, 52:185-194 (2005).

Winkler et al., "L-DOPA-Induced Dyskinea in the Intrastriatal 6-Hydroxydopamine Model of Parkinson's Disease: Relation to Motor and Cellular Parameters of Nigrostriatal Function," *Neurobiology of Disease*, 10: 165-186 (2002).

Wolf, "SLV-308 Solvay," *Curr Opin Investig Drugs*, 4: (2003).

Sharp, et al., Br. J. Pharmacol., "The novel 5-HT1A receptor antagonist, SDZ 216-525, decreases 5-HT release in rat hippocampus in vivo," 1993; 109: 699-702.

Corradetti, et al., Br. J. Pharmacol., "Antagonist properties of (−)-pindolol and WAY 100635 at somatodendritic and postsynaptic 5-HT1A receptors in the rat brain," 1998; 123: 449-462.

Marsden, CD et al (1977) Success and problems of long-term levodopa therapy in Parkinson's disease Lancet 1 (8007):345-349.

Mignon, LJ et al (2000) R-(+)-8-OHDPAT, a Serotonin 5-HT1A agonist, induces Ipsilateral Turning in the Unilateral 6-OHDA-Lesioned Rat Society for Neuroscience Abstracts vol. 30 Part 1 144.19.

Mir, AK et al (1988) MDL 72832: a potent and stereoselective ligand at central and peripheral 5-HT1A receptors Eur J Pharmacol 149(1-2):107-120.

Nelson, DL et al (1986) Spiroxatrine: a selective serotonin1A receptor antagonist Eur J Pharmacol 124(1-2):207-208.

Newman-Trancredi, A et al (1999) Actions of roxindole at recombinant human dopamine D2, D3 and D4 and serotonin 5-HT1A, 5-HT1B and 5-HT1D receptors Naunyn Schmiedebergs Arch Pharmacol 359(6):447-453.

Nomoto, M et al (1999) Effects of serotonin 5-HT1A serotonin receptor agonists on parkinsonism the Japanese Journal of Pharmacology vol. 79 Supplement I.

(56) References Cited

OTHER PUBLICATIONS

Oh, JD et al (1997) Protein kinase A inhibitor attenuates levodopa-induced motor response alterations in the hemi-parkinsonian rat Neurosci Lett 228(1):5-8.

Papa, SM et al (1994) Motor fluctuations in levodopa treated parkinsonian rats: relation to lesion extent and treatment duration Brain Res 662(1-2):69-74.

Papa, SM et al (1995) Reversal of levodopa-induced motor fluctuations in experimental parkinsonism by NMDA receptor blockade Brain Res 701(1-2):13-18.

Paul, M et al (1992) D1-like and D2-like dopamine receptors synergistically activate rotation and c-fos expression in the dopamine-depleted striatum in a rat model of Parkinson's disease J Neurosci 12(10):3729-3742.

Rinne, UK et al (1998) Entacapone enhances the response to levodopa in parkinsonian patients with motor fluctuations. Nomecomt Study Group Neurology 51(5):1309-1314.

Romero, AG et al (1993) Novel 2-substituted tetrahydro-3H-benz[e]indolamines: highly potent and selective agonists acting at the 5-HT1A receptor as possible anxiolytics and antidepressants J Med Chem 36(15):2066-2074.

Ruottinen, HM et al (1998) COMT inhibition in the treatment of Parkinson's disease J Neurol 245(11 Suppl 3):P25-34.

Savola, JM et al (2003) Fipamezole (JP-1730) is a potent alpha2 adrenergic receptor antagonist that reduces levodopa-induced dyskinesia in the MPTP-lesioned primate model of Parkinson's disease Mov Disord 18(8):872-883.

Smith, LA et al (1997) Entacapone enhances levodopa-induced reversal of motor disability in MPTP-treated common marmosets Mov Disord 12(6):935-945.

Stanton, JA et al (1997) Characterisation of a cloned human 5-HT1A receptor cell line using [35S]GTP gamma S binding Eur J Pharmacol 320(2-3):267-275.

Sweet, RD et al (1974) The "on-off" response to chronic L-DOPA treatment of Parkinsonism Adv Neurol 5:331-338.

Tanaka, H et al (1999) Role of serotonergic neurons in L-DOPA-derived extracellular dopamine in the striatum of 6-OHDA-lesioned rats Neuroreport 10(3):631-634.

Tetrud, JW et al (2004) A novel formulation of selegiline for the treatment of Parkinson's disease Neurology 63(7 Suppl 2):S2-6.

Tomiyama, M et al (2000) Effects of 8-OH-DPAT1A receptor agonist, on L-DOPA-Induced dyskinesisas in rats with nigrostriatal denervation Society of Neuroscience Abstracts vol. 30 Part 1 Abstract 278.10.

Tricklebank, MD et al (1985) The involvement of subtypes of the 5-HT1, receptor and of Catecholaminergic systems in the behavioural response to 8-Hydroxy-2-(Dl-n-Propylamino)Tetralin in the rat Eur J Pharmacol 106:271-282.

Wolff, MC et al (1998) Selective serotonin reuptake inhibitors potentiate 8-OH-DPAT-induced stimulus control in the pigeon Eur J Pharmacol 345(1):35-39.

Zhuang, ZP et al (1993) Synthesis of (R,S)-trans-8-hydroxy-2-[N-n-propyl-N-(3'-iodo-2'-propenyl)amino]tetral in (trans-8-OH-PIPAT): a new 5-HT1A receptor ligand J Med Chem 36(21):3161-3165.

Ba, M et al (2007) "Cellular and behavioral effects of 5-HT1A receptor agonist 8-OH-DPAT in a rat model of levodopa-induced induced motor complications," Brain Res.1127(1):177-184.

Benloucif, S et al (1991) "Facilitation of dopamine release in vivo by serotonin agonists: studies with microdialysis," Eur J Pharmacol 200:1-8.

Bezard, E et al (2013) "Study of the antidyskinetic effect of eltoprazine in animal models of levodopa-induced dyskinesia," Mov Disord. 28(8):1088-1096.

Blackburn, TP (1992) Chapter 8 "5-HT Receptor and Anxiolytic Drugs," Frontiers in Pharmacology & Therapeutics 175-197.

Bonifati, V et al (1994) "Buspirone in levodopa-induced dyskinesias," Clin Neuropharmacol 17(1):73-82.

Cedarbaum, JM et al (1991) "Early initiation of levodopa treatment does not promote the development of motor response fluctuations, dyskinesias, or dementia in Parkinson's disease," Neurology 41(5):622-629.

Cenci, MA et al (1998) "L-Dopa-induced dyskinesia in the rat is associated with striatal overexpression of prodynorphin- and glutamic acid decarboxylase mRNA," Eur J Neurosci 10(8):2694-2706.

CEREP Catalogue 2000.

Cotzias, GC (1969) "Modification of Parkinsonism—Chronic Treatment with L-Dopa," N Engl J Med 280(7):337-345.

Crossman, AR et al (1987) "Primate models of dyskinesia: the experimental approach to the study of basal ganglia-related involuntary movement disorders," Neuroscience 21(1):1-40.

Dourish, CT et al, ed. (1987) Ellis Horwood Ltd., Brain 5-HT1A Receptors Behavioural & Neurochemical Pharmacology.

Durif, F et al (1995) "Levodopa-induced dyskinesias are improved by fluoxetine," Neurology 45(10):1855-1858.

Durif, F (1999) "Treating and preventing levodopa-induced dyskinesias: current and future strategies," Drugs & Aging 14(5):337-345.

Duvoisin, RC (1974) "Variations in the "on-off" phenomenon," Adv Neurol 5:339-340.

Ebadi, M et al (2005), Parkinson's Disease, CRC Press ISBN 0-8493-1590-1595.

Eskow, KL et al (2007) "The partial 5-HT(1A) agonist buspirone reduces the expression and development of I-DOPA-induced dyskinesia in rats and improves I-DOPA efficacy," Pharmacol Biochem Behav 87(3):306-314.

Fabbrini, G et al (1987) "Levodopa pharmacokinetic mechanisms and motor fluctuations in Parkinson's disease," Ann Neurol 21(4):370-376.

Fahn, Stanley (2008) "How do you treat motor complications in Parkinson's disease: Medicine, surgery, or both?" Ann Neurol 64(Suppl):S56-S64.

Fanelli, RJ et al (1990) "Ipsapirone: a novel anxiolytic and selective 5-HT1A receptor ligand," Prog Clin Biol Res 361:461-467.

Fornal, CA et al (1996) "WAY-100635, a potent and selective 5-hydroxytryptamine1A antagonist, increases serotonergic neuronal activity in behaving cats: comparison with (S)-WAY-100135," J Pharmacol Exp Ther 278 (2):752-762.

Fox et al (1997) "Entacapone improves motor fluctuations in levodopa-treated Parkinson's disease patients," Ann Neurol 42(5):747-755.

Fox, SH et al (2002) "Stimulation of cannabinoid receptors reduces levodopa-induced dyskinesia in the MPTP-lesioned nonhuman primate model of Parkinson's disease," Mov Disord 17(6):1180-1187.

Fuller, RW et al (1986) "Central serotonin agonist actions of LY 165163, 1-(m-trifluoromethylphenyl)-4-(p-aminophenylethyl) piperazine, in rats," J Pharmacol Exp Ther. 239(2):454-459.

Giron, Jr. LT et al (1996) "Methods of managing levodopa-induced dyskinesias," Drug Safety 14(6):365-374.

Gottwald, MD et al (1997) "New pharmacotherapy for Parkinson's Disease," Ann Pharmacother 31(10):1205-1217.

Graham, WC et al (1990) "Autoradiographic studies in animal models of hemi-parkinsonism reveal dopamine D2 but not D1 receptor supersensitivity. II. Unilateral intra-carotid infusion of MPTP in the monkey (Macaca fascicularis)," Brain Res 514(1):103-110.

Hadrava V et al (1995) "Characterization of 5-hydroxytryptamine 1A properties of flesinoxan: in vivo electrophysiology and hypothermia study," Neuropharmacology 34(10):1311-1326.

Harrison, C et al (2003) The [35S]GTPgammaS binding assay: approaches and applications in pharmacology, Life Sci. 74(4):489-508.

Hauser, RA et al (2000) "A home diary to assess functional status in patients with Parkinson's disease with motor fluctuations and dyskinesia," Clin Neuropharmacol 23(2):75-81.

Hauser, RA et al (2004) "Parkinson's disease home diary: further validation and implications for clinical trials," Mov Disord 19(12):1409-1413.

(56) References Cited

OTHER PUBLICATIONS

Hauser, RA et al (2009) "Safety and tolerability of pardoprunox, a new partial dopamine agonist, in a randomized, controlled study of patients with advanced Parkinson's disease," Eur Neurol 62(1):40-48.

Henry, B et al (1998) "Characterization of enhanced behavioral responses to L-DOPA following repeated administration in the 6-hydroxydopamine-lesioned rat model of Parkinson's disease," Exp Neurol 151(2):334-342.

Hill, MP et al (2003) "Novel antiepileptic drug levetiracetam decreases dyskinesia elicited by L-dopa and ropinirole in the MPTP-lesioned marmoset," Mov Disord 18(11):1301-1371.

Hill, MP et al (2006) "Antiparkinsonian effects of the novel D3/D2 dopamine receptor agonist, S32504, in MPTP-lesioned marmosets: Mediation by D2, not D3, dopamine receptors," Mov Disord 21(12):2090-2095.

Iravani, MM et al (2006) "In 1-methyl-4-phenyl-1,2,3,6-tetrahydropyridine-treated primates, the selective 5-hydroxytryptamine 1a agonist (R)-(+)-8-OHDPAT inhibits levodopa-induced dyskinesia but only with increased motor disability," The Journal of Pharmacology and Experimental Therapeutics 319(3):1225-123.

Jones, CA et al (2010) "An in vivo pharmacological evaluation of pardoprunox (SLV308)—a novel combined dopamine D(2)/D(3) receptor partial agonist and 5-HT(1A) receptor agonist with efficacy in experimental models of Parkinson's disease," Eur Neuropsychopharmacol 20(8):582-593.

Kanda, T et al (1998) "Adenosine A2A antagonist: a novel antiparkinsonian agent that does not provoke dyskinesia in parkinsonian monkeys," Ann Neurol 43(4):507-513.

Kanda, T et al (2000) "Combined use of the adenosine A(2A) antagonist KW-6002 with L-DOPA or with selective D1 or D2 dopamine agonists increases antiparkinsonian activity but not dyskinesia in MPTP-treated monkeys," Exp Neurol 162(2):321-327.

Kannari, K et al (2001) "Activation of 5-HT(1A) but not 5-HT(1B) receptors attenuates an increase in extracellular dopamine derived from exogenously administered L-DOPA in the striatum with nigrostriatal denervation," J Neurochem 76(5):1346-1353.

Kannari, K et al (2002) [Tandospirone citrate, a selective 5-HT1A agonist, alleviates L-DOPA-induced dyskinesia in patients with Parkinson's disease] No To Shinkei 54(2):133-137.

Kimura, T et al (2000) "Effects of 8-OH-DPAT, a 5-HT1A receptor agonist, on L-DOPA-induced motor complications in 6-OHDA-Lesioned Rats," Neuroscience Research Abstract P-439.

Kostic, V et al (1991) "Early development of levodopa-induced dyskinesias and response fluctuations in young-onset Parkinson's disease," Neurology 41(2(Pt 1)):202-205.

Kurth, MC et al (1997) "Tolcapone improves motor function and reduces levodopa requirement in patients with Parkinson's disease experiencing motor fluctuations: a multicenter, double-blind, randomized, placebo-controlled trial," Neurology 48(1):81-87.

Lacivita, E et al (2008) "5-HT1A receptor, an old target for new therapeutic agents," Curr Top Med Chem 8 (12):1024-1034.

Larsson, LG et al (1990) "Different effects on the responses of functional pre- and postsynaptic 5-HT1A receptors by repeated treatment of rats with the 5-HT1A receptor agonist 8-OH-DPAT," Neuropharmacology 29(2):85-91.

Lindgren, HS et al (2007) "The "motor complication syndrome" in rats with 6-OHDA lesions treated chronically with L-DOPA: relation to dose and route of administration," Behav Brain Res 177:150-159.

Liu, H et al (1999) "A comparative study on neurochemistry of cerebrospinal fluid in advanced Parkinson's disease Neurobiol Dis," 6(1):35-42.

Löschmann PA et al (1992) "Motor activity following the administration of selective D-1 and D-2 dopaminergic drugs to MPTP-treated common marmosets," Psychopharmacology 09(1-2):49-56.

Hartog et al., "Eltoprazine hydrochloride." Drugs Future, vol. 13, pp. 222-223, 1988.

McCreary et al, "SLV308: a novel antiparkinsonian agent with antidepressant and anxiolytic properties." Solvay Pharmaceutical Conferences, vol. 1, pp. 51-58, 2002.

Vries et al., "Dose-proportionality of eltoprazine: Pharmacokinetics of single oral doses in healthy subjects," Euro. J. Clin Pharmacol., 41: 485-488 (1991).

\* cited by examiner

PHARMACOLOGICAL TREATMENT OF PARKINSON'S DISEASE

This application claims benefit of U.S. Provisional Application No. 60/777,939, filed on Feb. 28, 2006, herein incorporated by reference in its entirety.

This invention was made in part through funds from the Department of Veterans Affairs. As such, the United States government has certain rights in the invention.

FIELD OF THE INVENTION

The present invention relates to the co-administration of two neurotransmitter agonists to patients with motor disorders, for the purpose of symptom reduction. In particular the present invention provides methods and compositions for alleviation of akinesia, rigidity and/or tremor associated with Parkinson's disease.

BACKGROUND OF THE INVENTION

Parkinson's disease is a chronic, progressive, hypokinetic disorder characterized by impaired voluntary movement (See, Dale and Federman (eds.), WebMD *Scientific American Medicine*, NY: WebMD Corporation, Chapter 11, Section 15, pp. 1-21, 2001; Lang and Lozano, N Engl J Med, 339:1044, 1998; and Lang and Lozano, N Engl J Med, 339:1130, 1998). Parkinson's disease occurs as a result of the death of dopamine-producing neurons in the substantia nigra of the midbrain. Dopamine is a neurotransmitter, or chemical messenger, that transports signals to the parts of the brain that control movement initiation and coordination. The loss of dopamine in the brain is associated with multiple primary symptoms including: tremor of the hands, arms, legs, jaw, and face; rigidity or stiffness of the limbs and trunk; bradykinesia or slowness of movement; and postural instability or impaired balance and coordination.

Parkinson's disease afflicts more than one million persons in the United States alone (Lang and Lozano, supra, 1998), with approximately 50,000 new cases diagnosed each year. It is generally a disease of late middle age, with typical onset occurring at about age 60. About five percent of patients, however, have early-onset disease and are younger than 40 when symptoms begin.

Most current treatment strategies for Parkinson's disease (PD) focus on symptom control through one or more of medication, surgery, and physical therapy. The dopamine precursor, levodopa (L-DOPA) is still considered to be the gold standard in terms of treatment for PD (Schapira and Olanow, JAMA, 291:358-364, 2004). Unfortunately, L-DOPA can cause debilitating side effects (LeWitt and Nyholm Neurology, 62:S9-S16, 2004), including severe nausea, vomiting, and psychosis. Moreover, with prolonged use, patients frequently experience other side effects such as dyskinesias (spontaneous, involuntary movements) and "on-off" periods when the medication will suddenly start or stop working.

Surgical treatments are considered for patients with advanced disease or who have not responded adequately to medications. Accepted surgical treatments involve either the creation of small, precise lesions or the implantation of stimulating electrodes in specific brain regions that appear to be overactive in Parkinson's disease. More recently, implantation of fetal dopaminergic tissue has been utilized as a means of restoring dopamine levels in the brains of patients with Parkinson's disease (See, e.g., Freed et al., Arch Neurol, 47:505-512, 1990; and Lindvall et al., Science, 247:574-577, 1990). These types of methods, however, are highly invasive.

Thus, what is needed in the art are noninvasive treatment strategies for effectively controlling symptoms of Parkinson's disease and other movement disorders. In addition, it would be desirable to be in possession of therapy regimens that maximize the efficacy of existing medicines.

SUMMARY OF THE INVENTION

The present invention relates to the co-administration of two neurotransmitter agonists to patients with motor disorders, for the purpose of symptom reduction. In particular the present invention provides methods and compositions for alleviation of akinesia, rigidity and/or tremor associated with Parkinson's disease, as well as for alleviation of side effects associated with treatment associated with Parkinson's disease.

The present invention provides methods of treating a motor disorder, comprising: providing: i) a serotonin type 1A (5-HT1A) receptor agonist, ii) a dopamine receptor agonist, and iii) a subject diagnosed as having a motor disorder; and b) administering the serotonin type 1A receptor (5-HT1A) agonist to the subject during a pre-conditioning period; and c) co-administering the serotonin type 1A receptor (5-HT1A) agonist in combination with a low dose of the dopamine receptor agonist to the subject, under conditions suitable for reducing at least one symptom of the motor disorder, wherein the low dose of the dopamine receptor agonist is below that required for reducing at least one symptom of the motor disorder when administered in the absence of the serotonin type 1A (5-HT1A) receptor agonist. In some embodiments, the motor disorder is Parkinson's disease. In other embodiments, the motor disorder is parkinsonism arising from viral infection or drug use. In some preferred embodiments, the dopamine receptor agonist is not a dopamine precursor. In some embodiments, the serotonin type 1A (5-HT1A) receptor agonist is selected from the group consisting of arylpiperazines, azapirones, aminotetralins, and aminochromanes. In other embodiments, the serotonin type 1A (5-HT1A) receptor agonist is 8-hydroxy-2-(di-n-propylamino)tetralin (8OH-DPAT). In some preferred embodiments, 8OH-DPAT is administered via a transdermal patch. In some embodiments, the serotonin type 1A (5-HT1A) receptor agonist is selected from the group consisting of tandospirone, ipsapirone, gepirone, flibanserin, flesinoxan, sarizotan, repinotan and PRX-00023. In some preferred embodiments, the dopamine receptor agonist is a D1 type dopamine receptor agonist. In a subset of these embodiments, the D1 type dopamine receptor agonist is selected from the group consisting of SKF38393, SKF83959, SKF81297, SKF77434, SKF75670, SKF82958, and derivatives thereof. In further embodiments, the D1 type dopamine receptor agonist is selected from the group consisting of dihydrexidine, dinapsoline, A-77636, ABT-431, CY208-243, and A-68930. In other embodiments, the dopamine receptor agonist is a D2 type dopamine receptor agonist. In some of these embodiments, the D2 type dopamine receptor agonist is quinpirole. In other embodiments, the D2 type dopamine receptor agonist is selected from the group consisting of quinelorane, terguride, pergolide, talipexole, pramipexole, sumanirole, ropinirole, roxindole, bromocriptine, and cabergoline. In still further embodiments, the dopamine agonist is a dopamine precursor. In a subset of these embodiments, the dopamine precursor is levodopa (L-DOPA), which is administered with one or both of a L-aromatic amino acid decarboxylase inhibitor (e.g., carbidopa, benserazide, difluoromethyldopa, a-methyldopa, etc.) and a catechol-O-methyltransferase (COMT) inhibitor (e.g., tolcapone and entacapone). In still further embodiments one or both of the serotonin type 1A (5-HT1A) receptor agonist and the dopamine receptor agonist is a D1 type dopamine receptor agonist. In a subset of these embodiments, the serotonin type 1A (5-HT1A) receptor agonist is selected from the group consisting of sunipetron and aripiprazole. Also provided are methods further comprising administering a low dose of the dopamine receptor agonist to the subject during the pre-conditioning period, wherein the low dose is of the dopamine receptor agonist is below that required for reducing at least one symptom of the motor disorder when administered in the absence of the serotonin type 1A (5-HT1A) receptor agonist.

In some preferred embodiments, the present invention provides methods of treating Parkinson's disease, comprising: providing: i) a serotonin type 1A (5-HT1A) receptor agonist, ii) a dopamine receptor agonist, and iii) a subject diagnosed as having Parkinson's disease; and b) administering the serotonin type 1A receptor (5-HT1A) agonist to the subject during a pre-conditioning period; and c) co-administering the serotonin type 1A receptor (5-HT1A) agonist in combination with a low dose of the dopamine receptor agonist to the subject, under conditions suitable for reducing at least one symptom of Parkinson's disease, wherein the low dose of the dopamine receptor agonist is below that required for reducing at least one symptom of Parkinson's disease when administered in the absence of the serotonin type 1A (5-HT1A) receptor agonist. In some particularly preferred embodiments, the at least one symptom comprises one or more of bradykinesia, tremor, and muscle rigidity. Also provided are embodiments in which the co-administering the serotonin type 1A receptor (5-HT1A) agonist in combination with the dopamine receptor agonist to the subject is under conditions further suitable for reducing at least one side effect of the dopamine receptor agonist. In some preferred embodiments, the at least one side effect of the dopamine receptor agonist comprises dyskinesia (e.g., one or more of chewing, gnawing, twisting, tongue or mouth movements, head bobbing, and movements of the feet, hands, or shoulder). In other embodiments, the at least one side effect of the dopamine receptor agonist comprises a psychiatric disturbance (e.g., one or more of memory loss, anxiety, nervousness, agitation, restlessness, confusion, inability to sleep, nightmares, daytime tiredness, mental depression and euphoria). In some preferred embodiments, the dopamine receptor agonist is not a dopamine precursor.

Moreover, the present invention provides methods for treating a subject, comprising: providing; i) a serotonin type 1A (5-HT1A) receptor agonist, ii) a dopamine receptor agonist, iii) a subject receiving the dopamine receptor agonist for treatment of Parkinson's disease, wherein the subject is suffering from dopamine receptor agonist-induced dyskinesia; co-administering the serotonin type 1A receptor (5-HT1A) agonist in combination with the dopamine receptor agonist to the subject during a preconditioning period under conditions suitable for reducing the dopamine receptor agonist-induced dyskinesia; co-administering the serotonin type 1A receptor (5-HT1A) agonist in combination with the dopamine receptor agonist to the subject during a dosage optimization period, wherein dosage of the dopamine receptor agonist is gradually reduced until at least one symptom of the Parkinson's disease is re-emerges; and co-administering the serotonin type 1A receptor (5-HT1A) agonist in combination with the dopamine receptor agonist to the subject under conditions suitable for reducing the at least one symptom of the Parkinson's disease, while reducing the dopamine receptor agonist-induced dyskinesia, wherein dosage of the dopamine receptor agonist is below that of step b and above that of step c.

In addition, the present invention provides kits for treating Parkinson's disease comprising a serotonin type 1A (5-HT1A) receptor agonist, a dopamine receptor agonist, and instructions for administering the serotonin type 1A (5-HT1A) receptor agonist and the dopamine receptor agonist to a subject diagnosed as having Parkinson's disease, wherein the dopamine receptor agonist is administered at a dose below that required for reducing at least one symptom of the Parkinson's disease when administered in the absence of the serotonin type 1A (5-HT1A) receptor agonist. In some embodiments, the kit comprises a package (e.g., blister pack). In some preferred embodiments, the dopamine receptor agonist is not a dopamine precursor.

Also provided are compositions for treating Parkinson's disease comprising: a therapeutic dose of a serotonin type 1A (5-HT1A) receptor agonist and a subtherapeutic dose of a dopamine receptor agonist. In some preferred embodiments, the dopamine receptor agonist is not a dopamine precursor. In some particularly preferred embodiments, the compositions further comprise a pharmaceutically acceptable excipient.

DEFINITIONS

Figure 1:
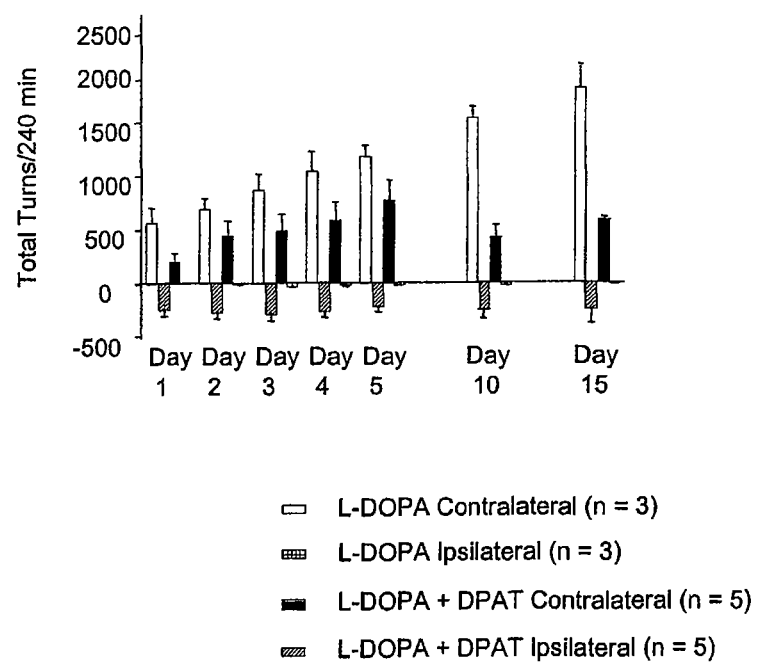
FIG. 1 depicts the effects of repeated daily dosing with L-DOPA (10 mg/kg+6.25 mg/kg benserazide) or L-DOPA plus R(+)-8-OHDPAT (0.3 mg/kg). Ipsilateral turning as well as contralateral turning was recorded and quantified.

To facilitate an understanding of the present invention, a number of terms and phrases are defined below:

The terms "Parkinson's disease," "Parkinson's" and "PD" refer to a neurological syndrome characterized by a dopamine deficiency, resulting from degenerative, vascular, or inflammatory changes in the basal ganglia of the substantia nigra. This term also refers to a syndrome which resembles Parkinson's disease, but which may or may not be caused by Parkinson's disease, such as Parkinsonian-like side effects caused by certain antipsychotic drugs. Parkinson's disease is also referred to as paralysis agitans and shaking palsy.

As used herein, the term "early stage of Parkinson's disease" refers broadly to the first stages in Parkinson's disease, wherein a person suffering from the disease exhibits mild symptoms that are not disabling, such as an episodic tremor of a single limb (e.g., the hand), and which affect only one side of the body.

In contrast, the term "advanced stage of Parkinson's disease" refers broadly to a more progressive stage in Parkinson's disease, wherein a person suffering from the disease exhibits symptoms which are typically severe and which may lead to some disability (e.g., tremors encompassing both sides of the body, balance problems, etc.). Symptoms associated with advanced stage Parkinson's disease may vary significantly in individuals, and may take many years to manifest after the initial appearance of the disease.

The terms "subject suffering from a Parkinson's disease" and "subject suffering from parkinsonism" as used herein, refer to both humans and animals displaying one or more symptom of Parkinson's disease. The primary symptoms of Parkinson's disease include bradykinesia, tremor, and muscle rigidity. The term "animals" refers to all non-human animals. Such non-human animals include, but are not limited to, vertebrates such as rodents, non-human primates, ovines, bovines, lagomorphs, porcines, caprines, equines, canines, felines, ayes, etc.

The terms "dopamine," "DA" and "4-(2-aminoethyl)benzene-1,2-diol," refer to a catecholamine neurotransmitter and hormone, formed first by the hydroxylation of the amino acid tyrosine to dihydroxyphenylalanine (dopa), and then by decarboxylation of dihydroxyphenylalanine (dopa) to dopamine. Dopamine is a precursor of adrenaline (epinephrine) and noradrenaline (norepinephrine).

The terms "serotonin," "5-hydroxytryptamine" and "5-HT" refers to a phenolic amine neurotransmitter produced from tryptophan by hydroxylation and decarboxylation in serotonergic neurons of the central nervous system and enterochromaffin cells of the gastrointestinal tract. Serotonin is a precursor of melatonin.

As used herein, the term "symptoms" refers to the outward manifestations of a disease. For instance, patients with Parkinson's disease exhibit symptoms such as bradykinesia, tremor, and muscle rigidity. Additional symptoms but are not limited to atypical gait, postural instability, and loss of balance.

The term "alleviating" refers to the act of providing relief from some painful state. As used herein, the term "alleviating" refers to the lessening of symptoms of Parkinson's disease or to the lessening of side effects associated with long term L-dopa administration. In some embodiments, the term "alleviating" comprises curing Parkinson's disease. In other embodiments, the term "alleviating" comprises decreasing the severity of the symptoms of Parkinson's disease as measured by any one of several accepted diagnostic measures including but not limited to UPDRS, Schwab and England Scale, and CAPIT.

The terms "Unified Parkinson's Disease Rating Scale" and "UPDRS" refer to a standardized tool used to measure Parkinson's Disease severity, as described by Fahn et al., in *Recent Developments in Parkinson's Disease*, Fahn et al. (eds.) Plurham Park, N.J.: Macmillian Healthcare Information, 2:153-163, 1987.

The term "Schwab and England Scale" refers to a standardized tool used to measure the efficacy of surgical treatment for Parkinson's Disease, as described by Schwab and England, in *Third Symposium on Parkinson's Disease*, Gillingham and Donaldon (eds.) Edinburgh, Scotland: Livingstone, pp. 152-157, 1969.

The terms "Core Assessment Program for Intracerebral Transplantation" and "CAPIT" refer to a standardized tool used to measure the efficacy of cerebral surgery, as described by Langston et al., Mov Disord, 7:2-13, 1992.

The terms "agonist" and "stimulator" refers to molecules or compounds that mimic the action of a "native" or "natural" compound. Agonists may be homologous to these natural compounds in respect to conformation, charge or other characteristics. Thus, agonists may be recognized by receptors expressed on cell surfaces. This recognition may result in physiologic and/or biochemical changes within the cell, such that the cell reacts to the presence of the agonist in the same manner as if the natural compound was present. The term "agonist" also encompasses the class of agents known as partial agonists, in which the maximal physiologic and/or biochemical changes that occur upon partial agonist administration may be less than the maximal effect exhibited by full agonists or the natural compound. In preferred embodiments, the term agonist refers to molecules that bind to and activate one or both of serotonin type 1A and dopamine type receptors.

As used herein, the terms "antagonist" and "inhibitor" refer to molecules or compounds that inhibit the action of a "native" or "natural" compound. Antagonists may or may not be homologous to these natural compounds in respect to conformation, charge or other characteristics. Thus, antagonists may be recognized by the same or different receptors than are recognized by an agonist. Antagonists may have allosteric effects, which prevent the action of an agonist. In contrast to the agonists, antagonistic compounds do not result in physiologic and/or biochemical changes within the cell, such that the cell reacts to the presence of the antagonist in the same manner as if the natural compound was absent.

As used herein the term "subtherapeutic dose" refers to a quantity of a neurotransmitter agonist (e.g., D1 agonist) below that used to treat disease when used as a monotherapy. In an exemplary embodiment, a subtherapeutic dose of a D1 agonist is equivalent to 5 mg of SKF38393 administered to an adult human subject four times a day.

As used herein, the term "therapeutic dose" refers to a quantity of a neurotransmitter agonist (e.g., 5-HT1A agonist)

used to treat disease (e.g., effect the cure of or that will correct the manifestations of a disease). In an exemplary embodiment, a therapeutic dose of a 5-HT1A agonist is equivalent to 5 mg of sarizotan administered to an adult human subject two or three times per day. In another exemplary embodiment, a therapeutic dose of a 5-HT1A agonist is equivalent to 5 mg of ipsapirone administered to an adult human subject four times a day.

DESCRIPTION OF THE INVENTION

The present invention relates to the co-administration of two neurotransmitter agonists to patients with motor disorders, for the purpose of symptom reduction. In particular the present invention provides methods and compositions for alleviation of akinesia, rigidity and/or tremor associated with Parkinson's disease.

Neurotransmitters

Parkinson's disease (PD) and related neurological disorders (e.g. postencephalitis parkinsonism, Hallervorden-Soatz disease) involve the progressive degeneration of dopamine neurons innervating the striatum. The loss of dopamine leads to excessive inhibition of thalamocortical motor activity, for which the primary manifestations are rigidity, bradykinesia, tremor and postural instability (Fahn, Ann NY Acad Sci, 991:1-14, 2003; and Hamani and Lozano, Ann NY Acad Sci, 991:15-21, 2003). The striatum is a major input structure that receives dense dopaminergic projections from the substantia nigra pars compacta and glutamatergic projections from the cortex and thalamus. Two efferent pathways originate in the striatum and utilize the inhibitory transmitter gamma-aminobutyric acid (GABA). The direct pathway is comprised of medium spiny striatonigral neurons that project directly to the output nuclei of the basal ganglia, which are the internal globus pallidus (rat homologue is the entopeduncular nucleus or EP) and the substantia nigra pars reticulata (SNr). These striatonigral neurons predominantly express dopamine $D_1$ receptors and co-express dynorphin and substance P (Gerfen, Clin Neuropharmacol, 18:S162-S177, 1995). The indirect pathway is comprised of medium spiny striatopallidal neurons that project to the external globus pallidus (GP). These striatopallidal neurons predominantly express dopamine $D_2$ receptors and co-express enkephalin (Gerfen, supra, 1995). The GP sends GABA projections to the subthalamic nucleus (STN), which in turn, sends glutamate projections to the EP and SNr. The EP and SNr serve as the final output structures of the basal ganglia and innervate the motor thalamus with inhibitory GABA projections. In PD and pre-clinical models of PD there is evidence of de-synchronization and hyperactivity in the STN, EP and SNr (Breysse et al., J Neurosci, 23:8302-8309, 2003; and Wichmann and DeLong, Ann NY Acad Sci, 991:199-213, 2003). Overactivity or dysregulated activity of these nuclei contributes to the motor deficits of PD.

Dopamine Replacement Therapy

The effects of $D_1$ agonists on striatonigral activity are somewhat controversial (Calabresi et al., Neurosci Biobehav Rev, 21:519-523, 1997). However, in the dopamine-denervated rat, $D_1$ agonists enhance the release of GABA within the SNr, as measured by in vivo microdialysis (You et al., Neuroscience, 63:427-434, 1994; and Trevitt et al., Psychopharmacol, 159:229-237, 2002). Increased GABA would be expected to reduce SNr inhibition to the thalamus and increase motor activity. Stimulation of $D_2$ receptors in the dopamine-denervated rat inhibits striatopallidal activity as a result of reducing glutamatergic activity from the cortex (Centonze et al., Clin Neurophysiol, 110:2006-2013, 1999). A downstream consequence of this action is a reduction in glutamate release from the STN projections in the output nuclei, which can be measured by in vivo microdialysis in the SNr or EP (Biggs et al., Brain Res, 753:163-175, 1997; and Biggs and Starr, Neurosci Biobehav Rev, 21:497-504, 1997). These techniques are contemplated to be useful for monitoring the effects on excitatory and inhibitory transmissions in the output nuclei of the anti-parkinsonian therapies of the present invention.

In the unilateral 6-hydroxydopamine (6-OHDA)-lesioned rat model of PD, 6-OHDA is used to selectively lesion dopamine neurons innervating the striatum on one side, thereby causing greater thalamic inhibition on the lesioned side (Schwarting and Huston, Prog Neurobiol, 50:275-331, 1996; and Deumens et al., Exp Neurol, 175:303-317, 2002). Agents that modify basal ganglia output manifest their effects as rotational behavior, the quantity and duration of which can be readily quantified. This model has also been used to assess the dyskinetic potential of drug treatments. Along these lines, a progressive increase in rotational response is observed upon repeated daily treatment with DA agonists or L-DOPA. This augmentation of behavior is often referred to as "priming" and has been taken as an index of dyskinetic potential, although there is currently considerable debate as to whether "priming" is exclusively indicative of motor complications (Di Chiara et al., Dev Pharmacol Ther, 18:223-227, 1992; and Henry et al., Exp Neurol, 151:334-342. 1998; Lane et al., Exp Neurol, 197:284-290, 2006; Marin et al., Exp Neurol, 197:269-274, 2006). Numerous studies have used this phenomenon to establish associations between the priming effect and neurobiological changes.

Selective $D_1$ agonists and selective $D_2$ agonists have demonstrated efficacy in rodent and primate models of PD (Schwarting and Huston, supra 1996; and Rascol et al., Ann Neurol, 45:736-741, 1999). However, only L-DOPA and $D_2$ agonists have found widespread use in treating PD (Jenner, Curr Opin Neurol, 16(S1):S3-S7, 2003). $D_2$ agonists have been utilized as monotherapy for mild or early stage PD and as adjuncts to L-DOPA in more advanced PD. If therapy is initiated with $D_2$ agonists alone, the incidence of dyskinesia is drastically reduced (Jenner, supra 2003). Unfortunately, $D_2$ agonists do not display the spectrum of efficacy seen with L-DOPA and as PD progresses L-DOPA therapy is frequently initiated (Jenner, supra 2003; and Lang and Lees, Mov Disord, 17(S4):S23-S37, 2002). Motor fluctuations and dyskinesias emerge as treatment with L-DOPA continues. It has been suggested that $D_1$ agonists may show a more favorable therapeutic profile than existing medications, but there has been little success with $D_1$ agonists for PD in the past (Emre et al., Mod Disord, 7:239-243, 1992; and Rascol et al., supra, 1999). There is a clear need to improve on drug therapy for PD.

The preferred dopamine receptor agonists for use with the present invention are partial agonists of the D1 dopamine receptor subtypes. Particular examples of such compounds are benzazepine derivatives such as SKF38393, SKF83959, SKF81297, SKF77434, SKF75670, SKF82958 (Pettersson et al., J Med Chem, 33:2197-2204, 1990; and Neumeyer et al., Eur J Pharmacol, 474:137-140, 2003). In some particularly preferred embodiments when given alone their anti-Parkinsonian action would be minimal or not evident. In further embodiments, full agonists of the D1 receptor are used. Examples of such compounds are tetrahydroisoquinoline derivatives such as dinapsoline (Ghosh et al., J Med Chem, 39:549-555, 1996), conformationally restricted phenanthridines such as dihydrexidine (Brewster et al., J Med Chem, 33:1756-1764, 1990), isochromans such as A68930, tetrahydroisoquinoline derivatives such as dinapsoline (Ghosh et al., J Med Chem, 39:549-555, 1996) and benzopyrans such as A-68930 and A-77636 (DeNinno et al., J Med Chem 33:2948-2950, 1990). However, in preferred embodiments full agonists of the D1 receptor are used at a significantly reduced dosage (e.g., at or below the threshold of clinical efficacy) as compared to the dosage used as monotherapy. In further embodiments, partial agonists of the D2 receptor subtype or full agonists of the D2 receptors are used (Jenner Curr Opin Neurol 16-[Suppl 1]:S3-S7, 2003; Bonucelli Curr Opin Neurol 16-[Suppl 1]:S13-S19, 2003), as described for D1 agonists.

Serotonin Adjuvant Therapy

The preferred serotonin (5-HT) receptor agonists for use with this invention are full agonists at the 5-HT1A receptor subtype, or partial agonists with moderate to high efficacy at the 5-HT1A receptor subtype. Particular examples of such compounds include phenylpiperazines such as flesinoxan, eltoprazine, ipsapirone, gepirone, tandospirone, buspirone, eltoprazine, befiperide, BMY7378, flibanserin, and aripiprazole (See, e.g., van Steen et al., J Med Chem, 36:2751-2760, 1993; van Steen et al., J Med Chem, 37:2761-2773, 1994; van Steen et al., J Med Chem, 38:4303-4308, 1995; Kuipers et al., J Med Chem, 38:1942-1954, 1995; Kuipers et al., J Med Chem, 40:300-312, 1997; and Heinrich et al., J Med Chem, 47:4684-4692, 2004). Particular examples also include substituted chromane derivatives such as sarizotan, 8-OHDPAT, alnespirone, BAY X 3702 (De Vry et al., J Pharmacol Exp Ther, 284:1082-1094, 1998; and Hammarberg et al., J Med Chem, 43:2837-2850, 2000) and pyridinemethylamine derivatives (Vacher et al., J Med Chem, 42:1648-1660, 1999).

Serotonin Preconditioning Period

The preconditioning period refers to the length of time required for pretreatment with a 5-HT1A receptor agonist (in the presence or absence of a dopamine agonist) before an anti-Parkinsonian effect is observed in response to combined 5-HT1A agonist-dopamine agonist therapy. This period is hypothesized to reflect the time required for neural changes to occur in response to the repeated 5-HT1A agonist administrations. Nonetheless, an understanding of the mechanism is not necessary in order to make and use the present invention. It is contemplated that a simple assessment of levels of the 5-HT metabolite 5-hydroxyindoleacetic acid (5-HIAA) in blood taken at the onset of 5-HT1A agonist treatment and following repeated 5-HT1A agonist administration (e.g., days to weeks) provides an indication as to whether the preconditioning period is adequate. For instance, a 20% or greater difference in 5-HIAA level between first and second sampling in which the 5-HIAA is lower at first sampling and the 5-HIAA level from the second sampling is anticipated to be in the range of 4.2-18.9 ng/ml (Yeung et al., J Pharm Sci, 85: 451-453, 1996) is contemplated to be indicative of sufficient preconditioning. Alternatively, a comparison of the plasma levels of cortisol and change in body temperature in response to the first administration of drug versus responses following drug administration after several weeks of treatment is also contemplated to be useful for assessing whether the preconditioning period is sufficient for effecting an anti-Parkinsonian response to subsequent combined 5-HT1A agonist-dopamine agonist therapy. For instance, an increase in plasma cortisol of 30% or greater and a reduction in body temperature of 0.2° C. or greater when assessed 90 minutes after drug intake is expected following initial 5-HT1A agonist treatment (Sargent et al., Psychopharmacol, 132:296-302, 1997; and Yatham et al., J Affect Dis, 54:295-301, 1999). It is contemplated that a significant attenuation of these responses will be seen when assessed 90 minutes following drug intake in patients that have received a sufficient preconditioning period of treatment (Sargent et al., Psychopharmacol, 132: 296-302, 1997).

EXPERIMENTAL

The following examples are provided in order to demonstrate and further illustrate certain preferred embodiments and aspects of the present invention and are not to be construed as limiting the scope thereof.

In the experimental disclosure which follows, the following abbreviations apply: U (units); N (normal); M (molar); mM (millimolar); µM (micromolar); mol (moles); mmol (millimoles); µmol (micromoles); nmol (nanomoles); pmol (picomoles); g (grams); mg (milligrams); µg (micrograms); ng (nanograms); l or L (liters); ml (milliliters); µl (microliters); cm (centimeters); mm (millimeters); µm (micrometers); nm (nanometers); ° C. (degrees Centigrade); OD (optical density); by (base pairs); PCR (polymerase chain reaction); RT (reverse transcriptase); DMEM (Dulbecco's modified Eagle medium); EDTA (ethylenediaminetetraacetic acid); FBS (fetal bovine serum); L-DOPA (levodopa); 6-OHDA (6-hydroxydopamine); and PBS (phosphate buffered saline).

Example 1

Motor Effects of Co-Administration of a Serotonin Agonist and L-DOPA in a Rat Model of Parkinson's Disease Preparation of Hemi-Lesioned 6-hydroxydopamine (6-OHDA)-Treated Rat Model of Parkinson's Disease.

Rats were rendered parkinsonian on one side of the brain by unilateral destruction of nigrostriatal dopamine neurons using the selective neurotoxin 6-OHDA and stereotaxic procedures. Animals were allowed to recover for at least 2 weeks following this procedure. Animals were then screened for efficacy of the lesion by subcutaneous injection of L-DOPA (25 mg/kg) plus the decarboxylase inhibitor benserazide (6.25 mg/kg) followed by assessment of motor activity.

Assessment of Motor Activity.

Anti-parkinsonian action in the hemi-lesioned 6-OHDA-treated rat model was assessed by the elicitation of rotational activity to the side opposite the lesioned hemisphere (contralateral turns) following drug treatment. The number of contralateral turns was assessed by videotape recording of animals and counting the number of turns.

Assessment of Dyskinetic Activity.

Observer assessment of motor dyskinesias was carried out be viewing the videotaped recording of rats during testing for rotational activity. A dyskinesia score was generated at 10 minute intervals throughout the course of the rotational test (generally 3 hr). Dyskinesia scores were based on the following scale: 0-no evidence of abnormal activity; 1 mild, intermittent forelimb dyskinesia; 2-severe, more persistent forelimb dyskinesia associated with animal directing activity toward forelimb; 3-severe limb and axial dyskinesia associated with loss of balance and consistent "barrel-rolling" activity. The dyskinesia scores that were obtained were averaged to generate a dyskinesia index.

Treatment and Results.

Rats that demonstrated contralateral turning indicative of a successful lesion received a daily subcutaneous injection of L-DOPA (10 mg/kg+6.25 mg/kg benserazide) or L-DOPA plus R(+)-8-OHDPAT (0.3 mg/kg). Ipsilateral turning as well as contralateral turning was recorded and quantified. As shown in FIG. 1, L-DOPA elicited almost exclusively contralateral turning, which became progressively greater upon repeated daily dosing. This represents the "priming" phenomenon, which may reflect neurobiological changes associated with L-DOPA-induced dyskinesias as well as an anti-Parkinsonian response (Lane et al., Exp Neurol 197:284-290, 2006). Although not quantified in this experiment, the turning response of L-DOPA-treated animals was observed to become progressively more uncoordinated upon repeated L-DOPA administration, suggesting the emergence of dyskinetic activity. Despite this, L-DOPA-treated animals turned approximately 3-fold more on Day 15 than on Day 1. Animals treated with L-DOPA plus R(+)-8-OHDPAT displayed ipsilateral turning early in the observation period (first 30 min) and then exhibited contralateral turning. The ipsilateral turning could be elicited by R(+)-8-OHDPAT treatment alone. Even so, contralateral turning elicited by L-DOPA plus R(+)-8-OHDPAT on Day 15 was approximately 2-fold greater than the contralateral turning exhibited on Day 1. Given that augmented turning can be used as an index of dyskinesia, the inventors cannot discount the possibility that rats receiving the combined treatment had displayed evidence of dyskinetic potential. However the inventors also noted that rats receiving the combined treatment turned in a much more natural, coordinated fashion. These observations are in line with a published report of reduced motor complications of levodopa treatment upon coadministration of the 5-HT$_1$A agonist sarizotan (Bibbiani et al., Neurology, 57:1829-1834, 2001).

Example 2

A Serotonin Agonist Enhances the Anti-Parkinsonian Actions of Dopamine Agonists in a Rat Model of Parkinson's Disease Treatment.

Hemi-lesioned 6-OHDA-treated rat that demonstrated contralateral turning indicative of a successful lesion were split into 2 groups that were balanced with respect to motor response to L-DOPA during screening. One group (controls) received a daily subcutaneous injection of vehicle (0.9% saline containing 0.1 mg/kg ascorbate; 1 ml/kg) for 14 days and the other group (8-OHDPAT) received a daily subcutaneous injection of R(+)-8-OHDPAT (0.3 mg/kg in 1 ml/kg volume) for 14 days. Beginning on day 15, both groups of rats were tested for motor activity and dyskinetic activity in response to the D1 receptor partial agonist SKF 38393 or the D2 receptor agonist quinpirole. Such testing was carried out in a randomized fashion with different doses of dopamine agonist being tested every $4^{th}$ day (e.g. 3 days between dopamine agonist administration). Throughout this testing phase the control group continued to receive daily injection of vehicle and the 8-OHDPAT group continued to receive daily injection of 0.3 mg/kg R(+)-8-OHDPAT. On days when dopamine agonists were tested the vehicle or R(+)-8-OHDPAT was administered simultaneously with the dopamine agonist.

Results.

Figure 2:
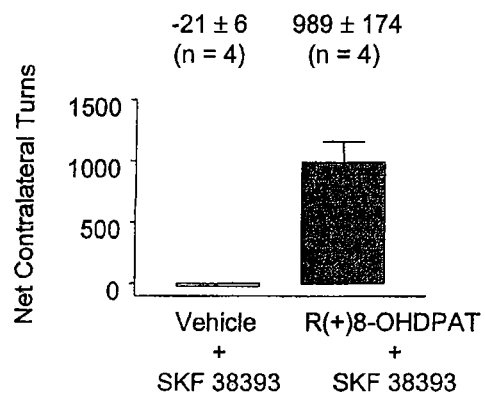
FIG. 2 demonstrates that a $5\text{-HT}_{1A}$ agonist enhances the anti-parkinsonian action of a $D_1$ type dopamine agonist as demonstrated by contralateral turning in the unilateral 6-OHDA-lesioned rat. The $5\text{-HT}_{1A}$ agonist R(+)-8-OHDPAT (0.3 mg/kg) or vehicle (0.9% saline containing ascorbate) was administered for 14 days. On Day 15, rats were given either vehicle or R(+)-8-OHDPAT (0.3 mg/kg), plus a low dose $D_1$ agonist SKF38393 (0.1 mg/kg) and observed for 3 hr.
Figure 3:
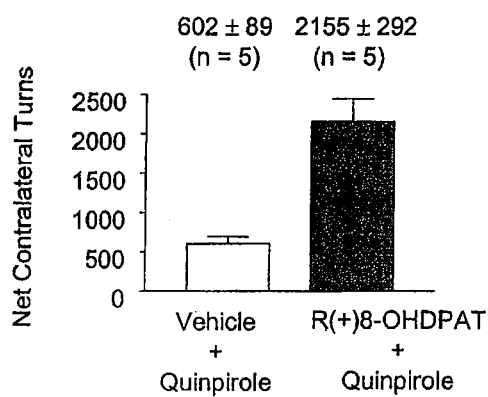
FIG. 3 demonstrates that a $5\text{-HT}_{1A}$ agonist enhances the anti-parkinsonian action of a $D_2$ type dopamine agonist as demonstrated by contralateral turning in the unilateral 6-OHDA-lesioned rat. The $5\text{-HT}_{1A}$ agonist R(+)-8-OHDPAT (0.3 mg/kg) or vehicle (0.9% saline containing ascorbate) was administered for 14 days. On Day 15, rats were given either vehicle or R(+)-8-OHDPAT (0.3 mg/kg), plus a low dose $D_2$ agonist quinpirole (0.05 mg/kg) and observed for 3 hr.

FIGS. 2 and 3 illustrate that administration of a 5-HT1A agonist enhances the anti-parkinsonian action of D1 and D2 agonists, as determined by quantitating contralateral turning in the hemi-lesioned 6-OHDA-treated rat. In both experiments animals were given the 5-HT1A agonist R(+)-8-OHDPAT (0.3 mg/kg) or vehicle (0.9% saline containing ascorbate) for 14 days. Rats that received R(+)-8-OHDPAT for 14 days were then given R(+)-8-OHDPAT (0.3 mg/kg) plus a dopamine agonist on test day, and were observed for 3 hr for anti-parkinsonian effect (contralateral turning). Rats that received vehicle for 14 days were then given a vehicle plus the dopamine agonist on test day, and were observed for 3 hr for anti-parkinsonian effect (contralateral turning). FIG. 2 depicts the data obtained when the D1 agonist SKF 38393 (0.1 mg/kg) was administered on test day. Animals that received R(+)-8-OHDPAT exhibited pronounced contralateral turning when SKF 38393 was administered. This turning behavior was significantly greater than what was observed for animals that received vehicle (p<0.005). In fact, animals that received vehicle plus SKF 38393 displayed no contralateral turning. FIG. 3 depicts the data obtained when the D2 agonist quinpirole (0.05 mg/kg) was administered on test day. Animals that received R(+)-8-OHDPAT exhibited significantly greater contralateral turning following quinpirole as compared to animals that received vehicle plus quinpirole (p<0.001).

Example 3

The Anti-Parkinsonian Effect of A Serotonin Agonist Requires Repeated Administration Repeated Administration of a 5-HT1A Agonist.

Figure 4:
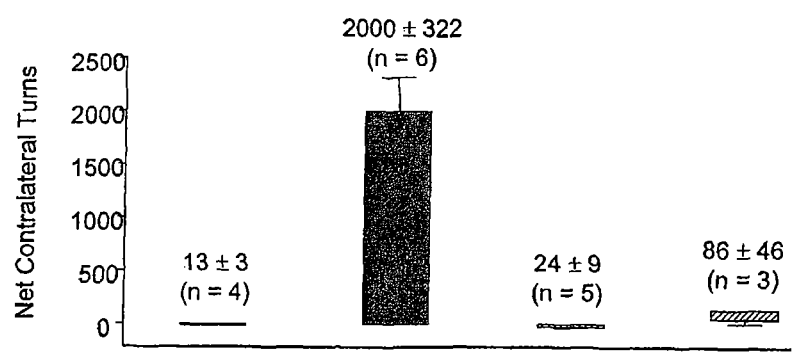
FIG. 4 illustrates that both repeated and concomitant administration of a serotonin agonist was required to enhance that anti-parkinsonian actions of a dopamine agonist.

The methods described in the previous examples were used to examine the effects of acute and chronic administration of the 5-HT1A agonist, R(+)-8-OHDPAT. The dose of both R(+)-8-OHDPAT and SKF 38393 was 0.3 mg/kg throughout this experiment. FIG. 4 graphically depicts the results of an experiment in which animals received either a) 14 days of R(+)-8-OHDPAT followed by SKF 38393 plus vehicle on test day, b) 14 days of R(+)-8-OHDPAT followed by SKF 38393 plus R(+)-8-OHDPAT on test day, c) 14 days of vehicle followed by SKF 38393 plus vehicle on test day, or d) 14 days of vehicle followed by SKF 38393 plus R(+)-8-OHDPAT on test day. Animals that received 14 day pretreatment with R(+)-8-OHDPAT plus concomitant R(+)-8-OHDPAT+SKF 38393 on test day exhibited significant anti-parkinsonian action greater than all other treatment groups (p<0.001). These data indicate that brain adaptations arising as a result of chronic treatment with R(+)-8-OHDPAT are necessary, but not sufficient, to enhance the anti-parkinsonian actions of dopamine agonists. These data also indicate that concomitant administration of a 5-HT1A agonist plus a dopamine agonist is necessary, but not sufficient, to enhance the anti-parkinsonian actions of dopamine agonists. Thus as determined during development of the present invention, both chronic and concomitant administration of a 5-HT1A agonist are required to achieve enhanced anti-parkinsonian actions.

Administration of a 5-HT1A Agonist Synergizes with a Low Dose DA Agonist.

Figure 10:
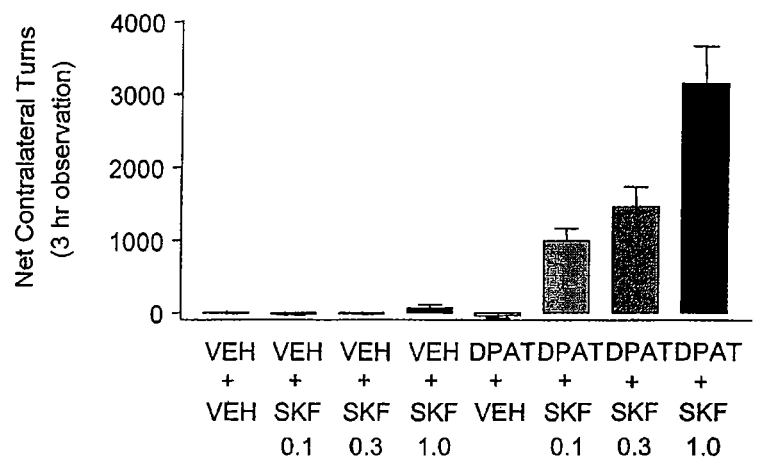
FIG. 10 depicts the rotational response in rats given once daily administration of vehicle+SKF 38393 (0.1, 0.3 or 1.0 mg/kg) for 15 days. Animals receiving once daily R(+)-8-OHDPAT (0.3 mg/kg) plus SKF 38393 displayed a significantly greater contralateral turning response that displayed a dose-dependency with respect to the dose of SKF administered.

Animals were unilaterally lesioned with 6-OHDA and allowed to recover and prescreened with L-DOPA (to assess extent of lesion) as described previously. FIG. 10 depicts the rotational response on day 15 in rats given once daily administration of vehicle+SKF 38393 (0.1, 0.3 or 1.0 mg/kg). There is little net contralateral turning by day 15 of treatment. In contrast, animals receiving once daily R(+)-8-OHDPAT (0.3 mg/kg) plus SKF 38393 treatments displayed a significantly greater contralateral turning response that displayed a dose-dependency with respect to the dose of SKF administered. These data clearly show the ability of a 5-HT1A agonist to synergize with an ineffective dose of a D1 agonist to elicit an anti-parkinsonian response.

Previous Exposure to a DA Agonist or L-DOPA is not Required.

Figure 11:
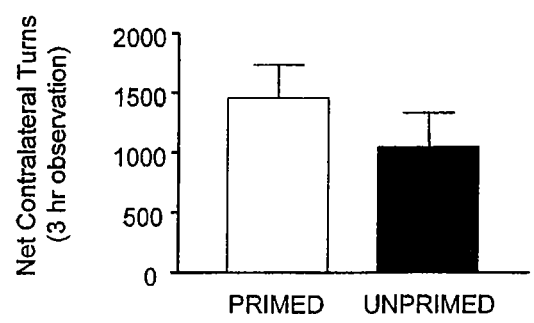
FIG. 11 compares the rotational response between pre-screened ("primed") and non-pre-screened ("unprimed") rats after 15 days of once daily administration of R(+)-8-OHDPAT (0.3 mg/kg) plus SKF 38393 (0.3 mg/kg). There is no significant difference between the groups.

Animals were unilaterally lesioned with 6-OHDA and allowed to recover as described previously. However, these animals were not pre-screened with L-DOPA prior to initiation of drug treatments. FIG. 11 compares the rotational response between pre-screened ("primed") and non-pre-screened ("unprimed") rats after 15 days of once daily administration of R(+)-8-OHDPAT (0.3 mg/kg) plus SKF 38393 (0.3 mg/kg). There is no significant difference between the groups. These data indicate that the methods and compositions of the present invention comprising combined 5-HT1A agonist and D1 agonist therapy will be effective in Parkinson's disease patients regardless of whether they have previously received treatment (e.g., DA agonist, L-DOPA or nothing).

Example 4

Figure 5:
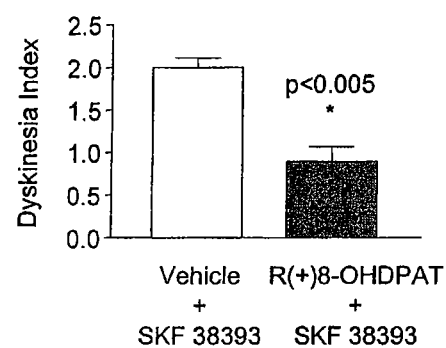
FIG. 5 demonstrates that repeated administration of R(+)-8-OHDPAT reduced dyskinetic behavior elicited by a moderately high dose of the $D_1$ agonist SKF 38393 (3.0 mg/kg).
Figure 6:
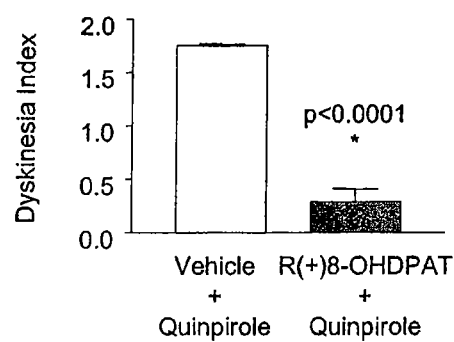
FIG. 6 demonstrates that repeated administration of R(+)-8-OHDPAT reduced dyskinetic behavior elicited by a moderately high dose of the $D_2$ agonist quinpirole (0.05 mg/kg).

A Serotonin Agonist Reduces Dyskinetic Behavior Elicited by Moderate Doses of Dopamine Agonists The experiments described in this example were conducted as described above. A dyskinesia index for each animal was determined during a 3 hr rotational test. FIG. 5 illustrates that repeated R(+)-8-OHDPAT administration reduced dyskinetic behavior elicited by a moderately high dose of SKF 38393 (3.0 mg/kg). Similarly, FIG. 6 illustrates that repeated R(+)-8-OHDPAT administration reduced dyskinetic behavior elicited by quinpirole (0.05 mg/kg).

Example 5

Figure 7:
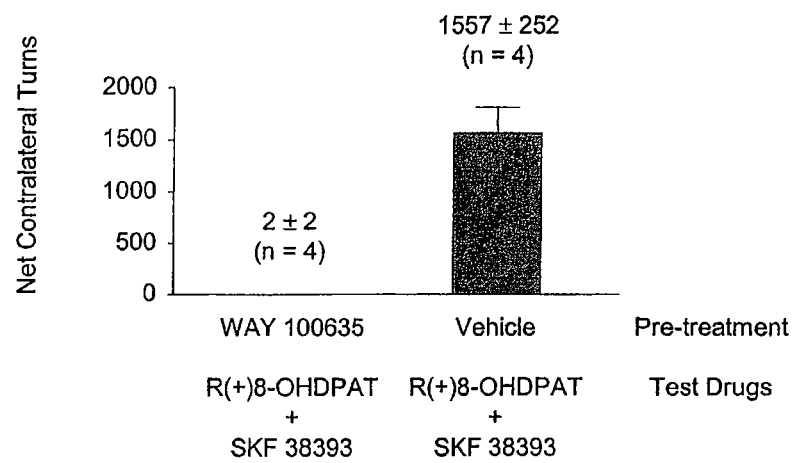
FIG. 7 illustrates that pre-treatment with a selective 5-HT1A antagonist (WAY 100635) blocked the facilitating effects of a serotonin agonist on the anti-parkinsonian action of a dopamine agonist.

The Anti-Parkinsonian-Enhancing Effect of R-(+)-8-OHDPAT is Mediated by the 5-HT1A Receptor The methods described in the previous examples were used to examine the effects of a selective 5-HT1A antagonist (WAY 100635) on the enhanced anti-parkinsonian action of a treatment regimen employing both R(+)-8-OHDPAT and SKF 38393. All animals received at least 14 days of daily R(+)-8-OHDPAT. FIG. 7 illustrates that pretreatment of animals on test day with WAY 100635 (0.1 mg/kg) prior to receiving R(+)-8-OHDPAT (0.3 mg/kg) plus SKF 38393 (0.3 mg/kg) blocked the facilitating effects of R(+)-8-OHDPAT on the anti-parkinsonian action of SKF 38393. These data confirm that the facilitating action of R(+)-8-OHDPAT is 5-HT1A receptor-mediated. Nonetheless, knowledge of the mechanism(s) is not necessary in order to make and use the present invention.

Example 6

Effects of Drug Treatment on Striatal Signaling

Transcription factors play a major role in mediating the long-term effects of synaptic plasticity by altering the expression of synapse-associated proteins. ΔFosB is a truncated splice variant of FosB that represents a long-lived transcription factor. ΔFosB has been shown to be upregulated following DA denervation in rodent and primate models of PD, as well as in PD patients (Cenci et al., Neuroscience, 94:515-527, 1999; Perez-Otano et al., Brain Res Mol Brain Res, 53:41-52 1998; and Tekumalla et al., Biol Psychiatry, 50:813-816, 2001). Repeated administration of L-DOPA or a $D_1$ agonist further elevates striatal ΔFosB, while $D_2$ agonists have no effect (Cenci et al., supra, 1999; Andersson et al., Neurobiol Dis, 6:461-474, 1999; and Doucet et al., Eur J Neurosci, 8:365-385, 1996).

Figure 8:
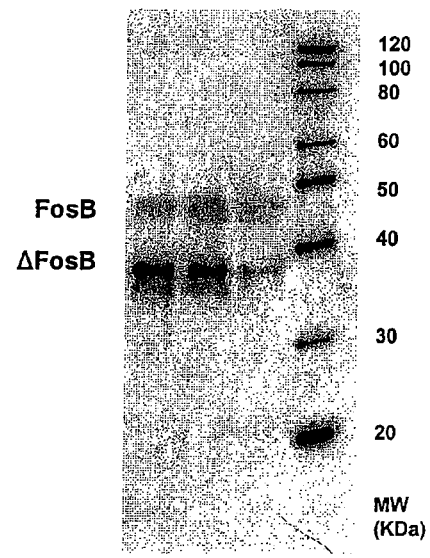
FIG. 8 is an image of an immunoblot of striatal extracts probed with an anti-Fos antibody.
Figure 9:
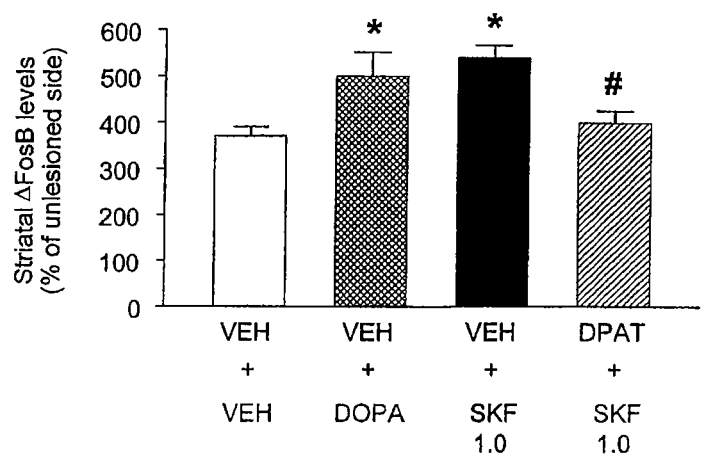
FIG. 9 illustrates that once daily administration of L-DOPA (25 mg/kg plus 6.25 mg/kg benserazide) or SKF 38393 (1 mg/kg) for 15 days elicits a significant increase in $\Delta$FosB in the denervated striatum of unilateral 6-OHDA-lesioned rats (*, significantly greater than vehicle-treated; $p<0.05$). The concomitant administration of the 5-HT1A agonist R(+)-8-OHDPAT (0.3 mg/kg) with SKF 38393 prevents the D1 agonist-induced rise in $\Delta$FosB (#, significantly less than VEH+SKF; $p<0.05$ and not significantly different from vehicle-treated).

To test whether a drug-related rise in ΔFosB contributes to dyskinesias elicited by repeated L-DOPA treatment, ΔFosB levels were assessed by immunoblotting. FIG. 8 provides an image of a typical blot. FIG. 9 illustrates that once daily administration of L-DOPA (25 mg/kg plus 6.25 mg/kg benserazide) or SKF 38393 (1 mg/kg) for 15 days elicits a significant increase in ΔFosB in the denervated striatum of unilateral 6-OHDA-lesioned rats (*, significantly greater than vehicle-treated; p<0.05). This figure also demonstrates that concomitant administration of the 5-HT1A agonist R(+)-8-OHDPAT (0.3 mg/kg) with SKF 38393 prevents the D1 agonist-induced rise in ΔFosB (#, significantly less than VEH+SKF; p<0.05 and not significantly different from vehicle-treated). Thus a significant target of the treatments of the present invention is contemplated to be ΔFosB in the striatum. Even so, knowledge of the mechanism(s) is not necessary in order to make and use the present invention.

Example 7

A Serotonin Agonist Enhances the Anti-Parkinsonian Actions of Dopamine Agonists in a Marmoset Model of Parkinson's Disease This example describes testing a serotonin agonist with a dopamine agonist in a nonhuman primate model of Parkinson's disease. Briefly, adult common marmosets (*Callithrix jacchus*) received either 0.9% saline SC (1 ml/kg) daily for five consecutive days (naïve controls) or MPTP (1-methyl-4-phenyl-1,2,3,6-tetrahydropyridine hydrochloride) SC (2 mg/kg) daily for five consecutive days. MPTP administration induces a motor disorder characterized by akinesia, bradykinesia and rigidity, which is relatively stable after an initial recovery period. Abnormal posture, loss of vocalization, diminished blinking, incoordination and a tremor are also frequently observed.

Efficacy of administration of a serotonin type 1A receptor agonist and a dopamine receptor agonist in reducing at least one symptom of MPTP-induced motor disorder is measured by behavioral assessment as described (Pearce et al., Psychopharmacol, 142:51-60, 1999). Briefly, automated locomotor counts, behavioral observation and dyskinesia scoring are recorded. Automated locomotor counts are taken through the use of cages equipped with multiple infrared photocells. The number of light beam interruptions caused by movement is enumerated in 10-min intervals over a 2-12 h and recorded by computer. An initial period of 30-60 min is used for habituation to the cages prior to drug dosing and behavioral assessment. The animals are also closely monitored by trained observers (e.g., a clinical neurologist with experience in movement disorders). The degree of motor dysfunction is scored on a disability grading system; alertness (normal/0, abnormal/1); reaction to stimuli (normal/0, reduced/1, slow/2, absent/3); blinking (normal/0, abnormal/1); checking movements (present/0, reduced/1, absent/2); posture (normal/0, abnormal trunk/+1, tail/+1, limbs/+1, grossly abnormal/4); balance (normal/0, unstable/1, spontaneous falls/2); motility (normal/0, mild slowing/1, moderate bradykinesia/2, akinesia/3); vocalisation (normal/0, reduced/1, absent/2); tremor (absent/0, present/1) fur condition (normal/0, dirty/1). These values are summed to yield a disability score out of 20. Disability scores are generated from continuous observation at half hour intervals before and during peak drug effect.

Abnormal movements are described according to classically defined criteria: chorea (rapid random kicking limb movements); athetosis (sinuous writhing limb movements); dystonia (abnormal sustained posturing); and stereotypy(repetitive purposeless or semipurposive movement). The presence of dyskinesias is scored at maximum drug effect employing a dyskinesia scoring system: 0=absent; 1=mild (fleeting and rare dyskinetic postures and movements); 2=moderate (more prominent abnormal movements, but not interfering significantly with normal behavior); 3=marked (frequent and at times continuous dyskinesias intruding upon normal repertory of activity); and 4=severe (virtually continuous dyskinetic activity, impairing the animal's normal behavior).

The inventors contemplate that administration of a serotonin receptor type 1A receptor agonist with a low-dose dopamine receptor agonist reduces motor dysfunction (reduces parkinsonian symptoms and/or dopamine-replacement therapy-induced dyskinesias) in MPTP-lesioned marmosets.

Example 8

A Serotonin Agonist Enhances the Anti-Parkinsonian Actions of Dopamine Agonists in a Parkinson's Disease Patients This example describes testing a serotonin agonist with a dopamine agonist in a human Parkinson's disease patients. Briefly, all patients admitted to this study are diagnosed with idiopathic Parkinson's disease (See, e.g., Gibb and Lees, J Neurol Neurosurg Psychiatry, 51:745-752, 1988).

Efficacy of administration of a serotonin type 1A receptor agonist and a dopamine receptor agonist in reducing at least one symptom of Parkinson's disease is measured using the United Parkinson's Disease Rating Scale (Fahn et al. (eds.), Recent Developments in Parkinson's Disease, vol. 2, New York, N.Y.: Macmillan Publishing Co. Inc., pp. 153-163 and 293-304, 1987), whereas dyskinesias are assessed using an art recognized severity scale (Marconi et al., Mov Disord, 9:2-12, 1994). Briefly, the dyskinesia severity scale rates abnormal movements from 0 (none) to 4 (severe with markedly impaired function) in six different parts of the body (face, neck and trunk, and four limbs).

The inventors contemplate that administration of a serotonin receptor type 1A receptor agonist with a low-dose dopamine receptor agonist reduces motor dysfunction (reduces parkinsonian symptoms and/or dopamine-replacement therapy-induced dyskinesias) in human Parkinson's disease patients.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention, which are obvious to those skilled in the relevant fields, are intended to be within the scope of the following claims.

We claim:

1. A method of reducing dyskinesia elicited by L-DOPA in a subject having Parkinson's disease treated with L-DOPA, said method comprising administering an amount of L-DOPA to said subject sufficient to provide an anti-Parkinsonian effect in said subject and wherein said method further comprises administering to said subject an amount of eltoprazine sufficient to reduce dyskinesia elicited by said L-DOPA.

2. The method according to claim 1, wherein said eltoprazine and said L-DOPA are concurrently active in said subject.

3. The method according to claim 1, wherein said eltoprazine is administered to said subject before administering L-DOPA.

4. The method according to claim 1, wherein after administering the eltoprazine and L-DOPA, subsequent doses of L-DOPA are reduced.

5. The method according to claim 1, wherein said subject is a human.

* * * * *